(12) United States Patent
Andersch

(10) Patent No.: US 8,026,409 B2
(45) Date of Patent: Sep. 27, 2011

(54) TAMPON

(76) Inventor: Björn Andersch, Sarö (SE)

( * ) Notice: Subject to any disclaimer, the term of this patent is extended or adjusted under 35 U.S.C. 154(b) by 790 days.

(21) Appl. No.: 11/885,957

(22) PCT Filed: Mar. 7, 2006

(86) PCT No.: PCT/EP2006/002059
§ 371 (c)(1),
(2), (4) Date: May 29, 2008

(87) PCT Pub. No.: WO2006/094753
PCT Pub. Date: Sep. 14, 2006

(65) Prior Publication Data
US 2009/0156979 A1    Jun. 18, 2009

(30) Foreign Application Priority Data
Mar. 9, 2005 (EP) .................................. 05005115

(51) Int. Cl.
*A61F 13/20* (2006.01)
(52) U.S. Cl. ... 604/383; 604/378; 604/363; 604/385.18; 604/904
(58) Field of Classification Search ............. 604/385.18, 604/904, 378, 383, 360, 363
See application file for complete search history.

(56) References Cited

U.S. PATENT DOCUMENTS

| | | | |
|---|---|---|---|
| 2,845,071 A | 7/1958 | Elmer | |
| 3,340,874 A * | 9/1967 | Burgeni | 604/379 |
| 3,491,758 A | 1/1970 | Mullan | |
| 3,712,305 A | 1/1973 | Wennerblom et al. | |
| 3,716,430 A | 2/1973 | Croon et al. | |
| 3,731,687 A | 5/1973 | Glassman | |
| 4,286,596 A * | 9/1981 | Rubinstein | 604/244 |
| 4,308,867 A * | 1/1982 | Roseman et al. | 424/431 |
| 4,342,314 A * | 8/1982 | Radel et al. | 604/370 |
| 4,543,098 A * | 9/1985 | Wolfe et al. | 604/370 |
| 5,688,257 A | 11/1997 | Olsen | |
| 6,177,606 B1 | 1/2001 | Etheredge et al. | |
| 6,359,191 B1 * | 3/2002 | Rusch et al. | 604/364 |
| 6,465,713 B1 * | 10/2002 | Gell et al. | 604/383 |
| 6,558,362 B1 * | 5/2003 | Chaffringeon | 604/287 |

(Continued)

FOREIGN PATENT DOCUMENTS

DE    44 05 174    6/1995

(Continued)

OTHER PUBLICATIONS

Hallberg, L. and L. Nilsson. "Determination of Menstrual Blood Loss." *Scandinav. J. Clin. & Lab. Investigation.* vol. 16, pp. 244-248 (1964).

(Continued)

*Primary Examiner* — Lynne Anderson
(74) *Attorney, Agent, or Firm* — Harness, Dickey & Pierce, P.L.C.

(57) ABSTRACT

A tampon comprising an absorbent core and a partially impermeable layer, where said absorbent core have a mantle area, an insertion end area, and a withdrawal end area is disclosed. The tampon further comprises an active layer, and said partially impermeable layer is arranged on at least a part of said mantle area, and said active layer is arranged on at least a part of said partially impermeable layer. The tampon will sustain a moistured surface layer, while at the same time excess fluid is distributed to the core of the tampon for storage.

18 Claims, 4 Drawing Sheets

U.S. PATENT DOCUMENTS

| | | | |
|---|---|---|---|
| 6,758,840 B2 * | 7/2004 | Knox | 604/385.18 |
| 2002/0143305 A1 * | 10/2002 | Yang et al. | 604/363 |
| 2002/0193722 A1 | 12/2002 | Maingault et al. | |

FOREIGN PATENT DOCUMENTS

| | | |
|---|---|---|
| GB | 1084177 | 9/1967 |
| GB | 1218641 | 1/1971 |
| WO | WO 03/043555 | 5/2003 |
| WO | WO 03/043557 | 5/2003 |

OTHER PUBLICATIONS

Hallberg, L. et al. "Menstrual Blood Loss—A Population Study." *Acta obst. et gynec. scandinav.* vol. 45, pp. 320-351 (1966).

Rybo, Göran. "Menstrual Blood Loss in Relation to Parity and Menstrual Pattern." *Acta. Obst. et gynec. scandinav.* vol. 45, Suppl. 7, pp. 25-45 (1966).

\* cited by examiner

TAMPON

TECHNICAL FIELD OF THE INVENTION

The present invention relates to an elongated tampon comprising an absorbent core, a partially impermeable layer and an active layer, said absorbent core having a mantle area, an insertion end area, and a withdrawal end area, where said partially impermeable layer is arranged on at least a part of said mantle area and said active layer is arranged on at least a part of said partially impermeable layer.

BACKGROUND ART

A wide variety of sanitary articles are known in the art for taking up menstrual fluid, e.g. sanitary towels (pads) and tampons. Sanitary towels have the drawback of being visible, since they are carried outside the body and also change position with body movements. Further, they may entail transfer of intestinal bacteria to the vagina. Many women therefore prefer tampons as protection against menstrual fluid, especially women who lead an active life.

During low production of menstrual fluid, the conventional tampon provides great friction which results in uneasiness to insert and withdraw as well as dryness of the vaginal mucosa. Women would prefer to use tampons exclusively if there are no side effects e.g. leakage, discomfort with insertion and withdrawal and no medical risks.

During the menstrual period women bleed on average 40 ml (1600 drops/5 days), and eighty percent of the total bleeding occurs during the first two days (106 drops/4 hours); thus during the three remaining days, women only bleed 8 ml (16 drops/4 hours). (Hallberg L, et al: Menstrual blood loss—A population study. Acta Obstet Gynecol Scand 45:320, 1966; Hallberg L, Nilsson L: Determination of menstrual blood loss volume. Scand J Clin Lab Invest 16:244, 1964; and Rybo, G, 1966, Menstrual blood loss in relation to parity and menstrual pattern, Acta Obstet Gynecol Scand 45 (Suppl7), 25-45).

Conventional tampons have an approximate maximal absorption capacity of 320 drops during the first second.

Hence, in view of the amount of menstrual fluid produced, conventional tampons have a significant overcapacity. The moisture balance in the vagina also supplies a moistured film to the vaginal mucosa. This moistured film is disturbed by use of a conventional tampon.

Moreover, the use of certain contraceptive agents, such as contraceptive pills, further reduces the amount of menstrual fluid during the menstrual period.

As a result of this major overcapacity, there is a great risk that the vaginal tissue will be dried out by the use of a tampon, especially during the later stage of the menstruation period. As a consequence, the risk for disturbances of the vaginal microbiota and the risk for infections is significantly increased.

A severe disease, which has appeared among tampon users, is called the toxic shock syndrome (TSS). TSS is caused by the uptake of bacterial toxins in the vaginal tissue. The risk for contracting TSS increases when the vaginal tissue is dried out, since then micro-wounds will easily result, which cause invasion of bacteria.

Accordingly, the overcapacity of conventional tampons is a great disadvantage which could impose severe medical risks to the users. Additionally, many women experience the friction of the tampon against the vaginal tissue as very discomforting, especially during insertion, withdrawal and use of the tampon.

In order to better adapt the absorption capacity of tampons to the actual need, tampons of different sizes have been produced, which shall be used during different stages of the menstrual period. However, the absorption capacity, even of the smallest available tampons, still widely exceeds what is required.

One example of a prior art tampon is disclosed in WO 03/043557, which describes a catamenial tampon comprising a generally absorbent member and a fluid wicking overwrap covering the absorbent member, said overwrap having an agar shear force of less than 90 grams. Since the agar shear force is less than 90 grams, this overwrap causes less discomfort for women by insertion, withdrawal and use of the tampon.

Until now, the problem with the overcapacity absorption of tampons has not been solved. There is therefore a great need for an improved tampon which does not adhere to the vaginal tissue or dry out the vagina, while leakage at the same time is avoided.

SUMMARY OF THE INVENTION

It is an object of the present invention to overcome the above-mentioned problems, by providing an improved tampon which does not dry out the vaginal mucosa.

The present invention provides an elongated tampon comprising an absorbent core, a partially impermeable layer and an active layer, said absorbent core having a mantle area and an insertion end area and a withdrawal end area. The partially impermeable layer is arranged on at least a part of said mantle area of said absorbent core, and said active layer is arranged on at least a part of said partially impermeable layer. In use, said partially impermeable layer in combination with said active layer has the ability to provide and maintain a wetted zone of said tampon, said wetted zone being in direct contact with the body or in contact with the body via an optional layer.

Due to this particular arrangement of the impermeable layer, the active layer will accumulate liquid and store menstrual fluid during use to establish a wetted zone, and the absorption rate will thus be controlled, so that the vaginal mucosal area not will be dried out. With the use of a tampon of the present invention, the moistured film of the vaginal mucosa will furthermore be re-established. This effect will be further described below.

The partially impermeable layer may comprise a plastic foil or a non-woven material. The partially impermeable layer may contain openings, which may be obtained mechanically, e.g. by perforation. The openings may be distributed homogenously or irregularly over the surface of the partially impermeable layer. The sum of the area of the openings may e.g. constitute from 0.1 to 15% of the total area of said impermeable layer. It may also constitute from 0.5 to 10% or from 1 to 5% of the total area of said impermeable layer.

By using such a partially impermeable layer, a slower absorption of fluid from the active layer to the absorbent core will be achieved, thereby reducing the absorbent overcapacity of the absorbent core. Furthermore, the partially impermeable layer constitutes a partial barrier for the fluid, and excess fluid will be distributed to the core of the tampon for storage. However, the inventive improved tampon has the same high volume absorption capacity as the conventional tampon.

The partially impermeable layer may also cover the withdrawal end area of the tampon. Where the partially impermeable layer covers the withdrawal end area, in one embodiment of the invention the partially impermeable layer does not contain openings at the withdrawal end area. Thereby, the fluid absorbed in the core will be retained there, and the tampon will not leak.

An overwrap may be arranged to cover the active layer and the insertion and withdrawal end areas. The overwrap may comprise a non-woven material. By arranging the overwrap in such a way to cover the tampon, the risk that small fibers stick to the vaginal tissue and cause irritation is decreased. Moreover, the surface area of the tampon will give a cleaner appearance and will be easy to handle after withdrawal.

The active layer may comprise a fluid retaining material, such as goretex, viscose, a hydrofil non-woven material, wettex or a fungi material.

The active layer may be loaded with an active composition. Due to the partially impermeable layer, which does, despite the high absorption capacity of the core, prevent absorption of the active composition from the active layer to the absorbent core, the active composition will more easily be administered to the vaginal tissue instead of being absorbed into the absorbent core.

The active composition may e.g. comprise polyethylene glycol (PEG) or witepsol, hypromellosum and wecobee, and optionally further comprise a medical composition. The medical composition may e.g. comprise lactic acid or other acidic substances with a pH of 3.8-4.5. By using PEG, a lubricating effect will be achieved, which will facilitate insertion and withdrawal of the tampon. The lactic acid is pH reducing, and thus inhibits pathogens, and further favors useful bacteria in the vagina.

The menstrual bleeding is adverse for the normal vaginal microbiota because of the alkalinization of the vaginal fluid. The odour produced by this alkalinization can be reduced by addition of a strong acid. Lactic acid is a strong acid and thus suitable to lower vaginal pH. Hence, lactic acid furthermore has an odor reducing effect.

Other objects and advantages of the present invention will be apparent to the skilled man in conjunction with the accompanying description and drawings.

DETAILED DESCRIPTION OF PREFERRED EMBODIMENTS OF THE INVENTION

The present invention will now be described in more detail with reference to the accompanying schematic drawings.

Figure 1:
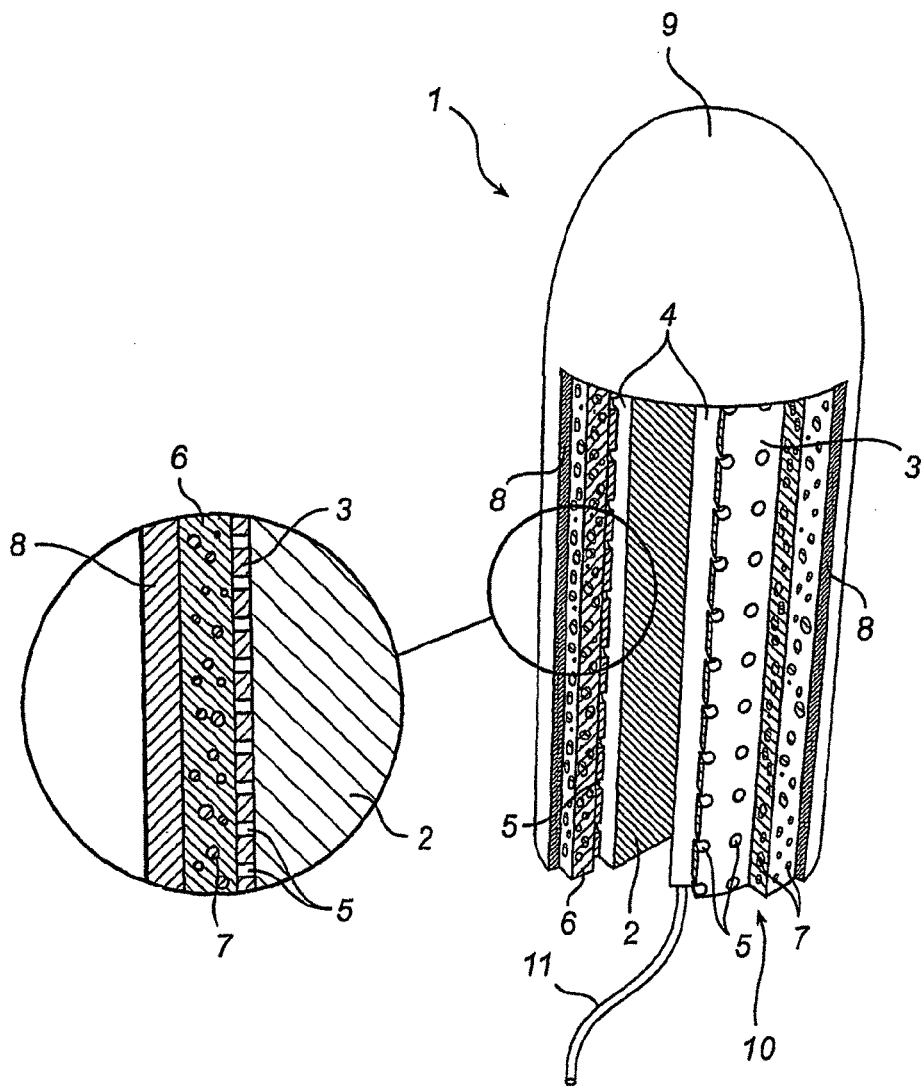
FIG. 1 shows a three dimensional view of a tampon according to the invention.

With reference to FIG. 1, there is shown a tampon 1 according to an embodiment of the present invention. The tampon is generally elongated with a tubular form that extends to a rounded insertion end area 9. The tampon 1 comprises of a high absorbent core 2, which preferably is made of cotton, or other high absorbent capillary fiber material.

The partially impermeable layer 3 is arranged on the mantle area 4 of the absorbent core 2. It may cover the mantle area 4 completely, or it may cover a smaller part of the area.

"A partially impermeable layer" as used herein refers to a layer that does not allow fluid to pass through the layer without resistance. The partially impermeable layer 3 may comprise a material which is almost completely impermeable to fluid, e.g. a plastic material, and which has been modified to comprise openings 5. This may be achieved by mechanical alteration, for example by aperturing or perforation. The sum of the area of the openings may e.g. constitute from 0.1 to 15% of the total area of said impermeable layer 3. It may also constitute from 0.5 to 10%, from 1 to 5%, from 5 to 10% or from 2 to 6% of the total area of said impermeable layer 3. The openings 5 may have any form, for example oval or circular. In the case of essentially circular openings, their diameter is in the range of from 0.5 to 3 mm.

For example, the partially impermeable layer 3 may comprise a non-woven material or other material which may allow some of the fluid to pass through the layer. By modifying the layer to comprise openings 5, the permeability of the layer can be adjusted.

The openings 5 may be uniformly distributed over the mantle area 4 of the partially impermeable layer 3. By "uniformly distributed" over the area of the partially impermeable layer 3 is meant that the openings 5 are spaced apart at certain intervals. However, in another embodiment, the openings 5 may be irregularly distributed over the mantle area 4 of the partially impermeable layer 3.

In one embodiment, the elongated tampon comprises an absorbent core, a partially impermeable layer and an active layer, said absorbent core having a mantle area and an insertion end area and a withdrawal end area. The partially impermeable layer is arranged on at least a part of said mantle area of said absorbent core, and said active layer is arranged on at least a part of said partially impermeable layer. The partially impermeable layer contains openings, in such a way that the sum of the area of the openings may e.g. constitute from 0.1 to 15% of the total area of said impermeable layer. It may also constitute from 0.5 to 10%, from 1 to 5%, from 5 to 10% or from 2 to 6% of the total area of said impermeable layer 3.

An active layer 6 is arranged on the partially impermeable layer 3. It may cover the area completely, or it may cover a smaller part of the area.

The term "active layer" as used herein refers to a layer which absorbs fluid, and thereby said layer maintains a moistured surface, which will not be dry. The active layer 6 may comprise a viscose layer, a cotton layer, a hydrophilic non-woven material or any combination thereof. It may also comprise a fluid retaining material, such as GORETEX, viscose, a hydrophilic non-woven material, WETTEX or fungi material.

"A wetted zone" as used herein refers to a zone in the active layer, which zone is wetted. The wetted zone is established by the partially impermeable layer in combination with the active layer, wherein the wetted zone may be in contact with the body. The wetted zone may also be in contact with the body via an optional layer. Such an optional layer may be an overwrap.

The wetted zone is established following that in use, the liquid absorbed into the active layer will first partly be distributed in said active layer, before the liquid is absorbed through the partially impermeable layer into the absorbent core of the tampon.

Figure 5:
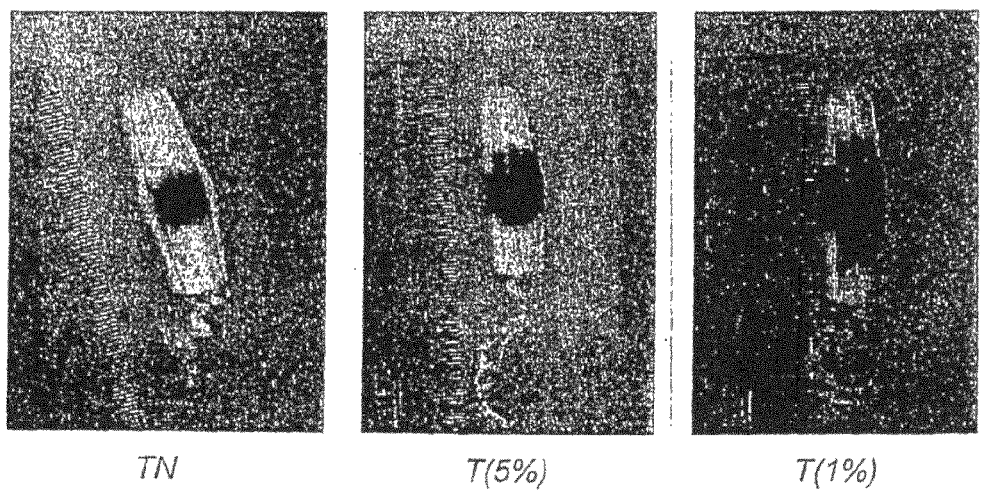
FIG. 5 shows the absorption spread of 10 drops of fluid on the surface of the different tampons. From the left: TN, T(5%), T(1%).

Examples of wetted zones are seen in FIG. 5. In FIG. 5, it is clear to see that the total sum of the area of the openings of the impermeable layer affect the size if the wetted zone. Thus, the smaller the total sum of the area of the openings of the impermeable layer is, the more the fluid is distributed in the active layer, and the larger is the size of the wetted zone.

The active layer may contain an added active composition 7, to be administered to the vaginal tissue, distributed in the active layer.

The active composition may comprise a carrier, optionally loaded with an active composition, or a medical composition. The carrier may be PEG, witepsol, hypromellosum and WECOBEE. The medical composition may be an acidic substance with a pH of 3.8-4.5, lactic acid, a metal, for example zinc, magnesium; lactic acid bacteria, lactoferrin or an antifungal composition. A medical composition may comprise of a single substance. Thus, a tampon according to the invention with such an active composition may be used as an administrator of medical composition. It may even be used as a means of administration of a medical composition when the female is not menstruating due to the fact that the tampon does not dry out the mucous membrane.

An overwrap 8 may be arranged to cover the active layer and the insertion end area 9 and the withdrawal end area 10, i.e. to cover the entire tampon. The overwrap 8 may comprise a non-woven material.

The tampon may be pulled out by means of a pull out string 11.

Figure 2:
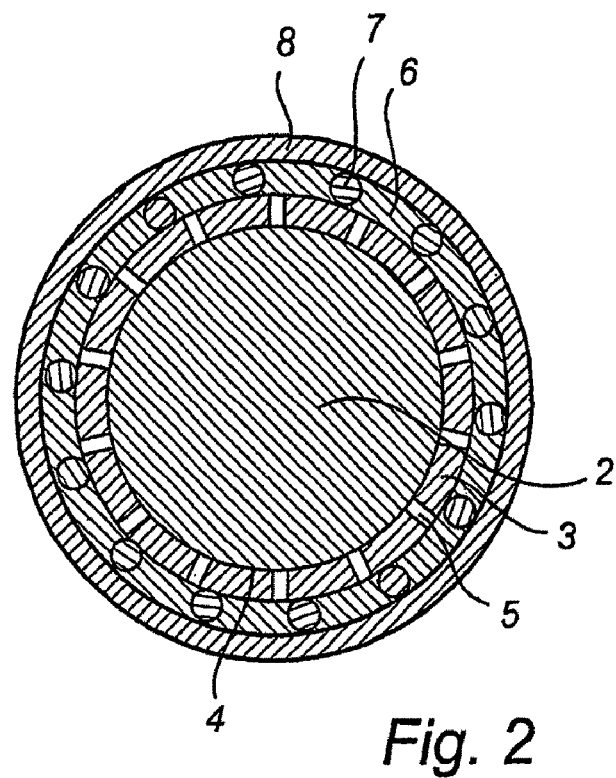
FIG. 2 shows a cross sectional view of a tampon according to the invention.

With reference to FIG. 2, there is shown a cross section of an embodiment of the present invention.

The overwrap 8 is arranged on the active layer 6, which active layer may comprise an active composition 7. The active layer 6 in turn is arranged on the partially impermeable layer 3, said partially impermeable layer 3 may comprise openings 5. The partially impermeable layer 3 is arranged on a mantle area 4 of an absorbent core 2.

Figure 3:
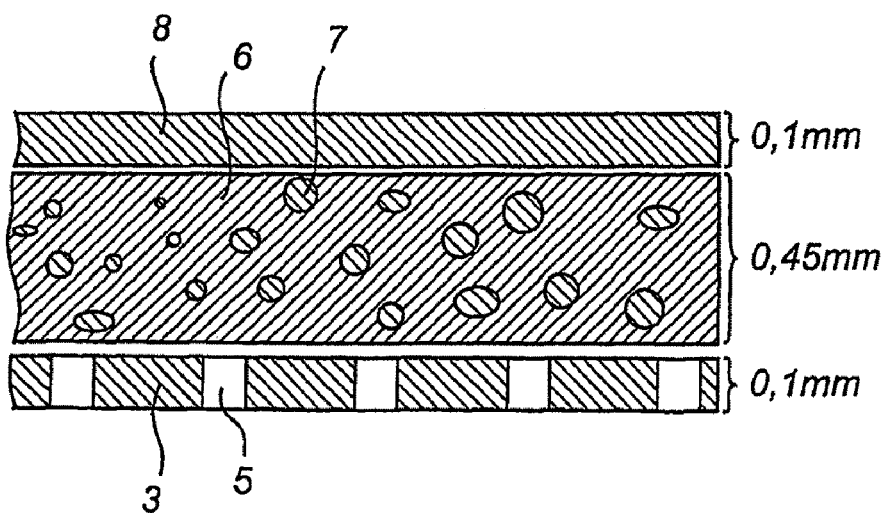
FIG. 3 shows an exploded radial cross section of a tampon according to the invention.

With reference to FIG. 3, there is shown an exploded cross section of an embodiment of the present invention. The overwrap 8 is arranged on the active layer 6, which in turn is arranged on the partially impermeable layer 3. The active layer may comprise an active composition 7, and the partially impermeable layer may comprise openings 5.

In the following, typical function of a tampon 1 according to the invention is described in more detail.

After insertion in the vagina of the tampon of the present invention, the tampon will expand to fill up the space of the vagina. As body fluid (menstrual fluid or leucorrhoea) reaches the tampon, it will be absorbed by the overwrap 8. As more fluid reaches the surface area of the tampon, it will be absorbed through the overwrap in to the active layer 6, and the tampon will start to expand. The partially impermeable layer 3 will retain and distribute the fluid in the active layer until the active layer has been saturated. After saturation of the active layer, the fluid will be absorbed through the partially impermeable layer into the absorbent core of the tampon.

Thus, the active layer of the tampon will create a moistured surface against the vaginal tissue, while excess fluid will be absorbed by the absorbent core, through the partially impermeable layer. Therefore, the tampon will not release or resubmit excess fluid as the tampon is exposed to increased pressure during withdrawal or compression of the tampon, since the partially impermeable layer will form a barrier, which retains the absorbed fluid in the absorbent core.

The partially impermeable layer may be arranged to also cover the withdrawal end area of the tampon. As an effect, the fluid absorbed into the core will stay in the core. Fluid may on the other hand freely be absorbed through the insertion end area of the tampon in to the absorbent core. In one embodiment of the invention, the part of the partially impermeable layer which covers the withdrawal end area of the tampon may contain no openings, so that the fluid is retained in the core and cannot leak through this layer.

The active layer, the partially impermeable layer and the overwrap will constitute a thin layer as compared with the core. The overwrap may for example be from 0.01 to 1, more preferably from 0.1 to 0.5 mm, the active layer from 0.1 to 0.45 or from 0.45 to 1 mm and the partially impermeable layer from 0.01 to 1, more preferably from 0.1 to 0.5 mm.

The diameter of the absorbent core will preferably be such that the diameter of the tampon does not differ much from conventional tampons. The core may hence be from 8 to 12 mm in diameter.

Further, the partially impermeable layer as well as the active layer and the overwrap suitably expand as the core expands.

The active layer may be loaded with an active composition. As the overwrap and the active layer is saturated by fluid, the active composition will be released to the vaginal tissue. Due to the initial limited absorption of the absorbent core (as stated above, because of the partially impermeable layer which will prevent excessive absorption), the active composition will not be absorbed back in to the tampon after administration to the vagina.

Tampons have been used to administer medically active compositions in the vagina. Another method for performing this is by using a so called vaginal insert, which is a substance, normally with an oval shape, consisting of a substance melting at body temperature. Said substance is a carrier of an active composition. However, this method of administration has the disadvantage that the melted carrier simply will leak from the vagina, and the active composition will thus not be utilized in the vagina. This will also entail some hygienic problems.

In order to avoid these problems, use of an absorbent tampon has been suggested. The tampon may either be impregnated by a carrier and/or an active substance, or may be provided with a top of the composition of the vaginal insert. In this way, the tampon will keep the carrier and/or active substance in the vagina. These suggestions however result in that the absorbent tampon will absorb the active substance, and the active substance will not be effectively administered to the vagina. In order to achieve an optimal result in regard of administration of an active composition, the present inventive tampon however has a well-suited absorption, and is thus very suitable for use to administrate an active composition.

In one embodiment, the tampon of the present invention has a completely impermeable layer. According to this embodiment, the active layer is provided with an active composition and/or a medical composition, and the tampon is used for administering said active composition and/or a medical composition. As explained above, administration of such a composition by using the inventive tampon with an impermeable layer will result in that said composition will be appropriately utilized in the vagina.

As earlier described, the menstrual bleeding is adverse for the vaginal balance, since the bleeding is alkaline and the natural defence of the vagina is based on an acid environment. Thus, studies have shown that administration of lactate to the vagina enforces the natural defence of the vagina. As a consequence, lactate is suitable to administer at menstruation.

The active composition may comprise a carrier, which is optionally loaded with a medical composition. The carrier has a lubricating effect and may therefore be used alone. The carrier may also be added since it is a vehicle to be used for administration of the medical composition. The acidic substance is preferably added with a carrier. PEG is relatively solid at room temperature and in a dry environment and thus may form an article, but melts at body temperature, and in contact with body fluid, and will thus release the active composition.

In the following, the invention will now be illustrated further through non-limiting examples.

EXAMPLES

Absorption Tests
Materials

A number of absorption tests were performed in order to evaluate the absorption of different kinds of material combinations. The tests were performed with four different material combination possibilities:
1. Material combination without plastic film.
2. Material combination with plastic film without openings.
3. Material combination with plastic film with 1% of the total area perforated.
4. Material combination with plastic film with 10% of the total area perforated.

The plastic film used was ME0385 White, 0.022 mm thick, from Trioplanex International AB. In the material combination with plastic film with 1% of the area perforated, the plastic film was perforated with openings of 0.65 mm in diameter. In the material combination with plastic film with 10% of the area perforated, the plastic film was perforated with openings of 2 mm in diameter. The other materials making up the tampon were obtained from conventional tampons (from Apoteket).

Example 1

Measurements were made of the water absorption at a pressure of 2.5 kPa. The tampon was placed on a filter connected to a water supply. The absorption of water was measured as the amount of absorbed water over time. The tests were performed by 5 samples per combination, conditioned to 20° C., 65% RH. One of the sample contained addition of 15 drops of PEG to the active layer of the material combination perforated to 1% by openings. The tests were discontinued when the absorption did not exceed 1% of the maximal absorption within 5 seconds.

Figure 4:
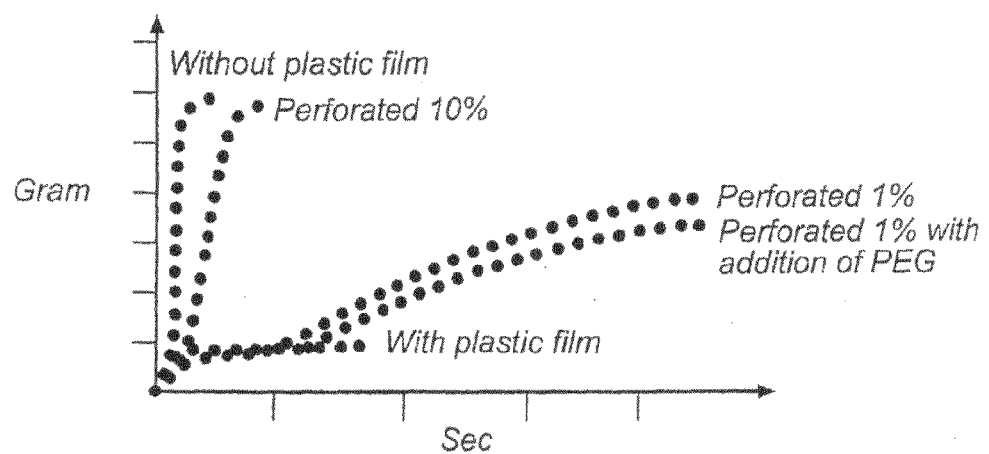
FIG. 4 shows the absorption of fluid over time for the different material combinations.

As can be seen from FIG. 4, the amount of water absorbed over time differs between the different material combinations. The absorption rate of the material combination containing a plastic film with an area perforated 10% does not differ much from the material combination without plastic film. On the other hand, the absorption rate of the material combination with the plastic film with 1% openings is much reduced. The addition of PEG to the sample also reduces the absorption rate. Thus, it is clear that the excessive absorption capacity can be controlled by a plastic film with openings.

Example 2

In order to measure the absorption rate under pressure, the SYNGINA TEST METHOD No 350.=–99 was used. The method aims at imitating the environment in the vagina. This is achieved by using a condom in a filled water chamber.
Material Three different types of tampons were used. As a reference, a tampon of prior art (TN) produced by San Point AB was used, comprising of a highly absorbent core of cotton fibers, covered by a 0.1 mm non-woven overwrap.

The tests examples were tampons according to the invention, with an absorbent core, and a partially impermeable layer arranged on at least a part of said mantle area of said absorbent core, and said active layer being arranged on at least a part of said partially impermeable layer (see FIG. 1). The partially impermeable layer comprised of an almost water impermeable non-woven layer which had openings of 1 mm diameter according to the following;
T(1%): Perforated layer of 25 openings/cm$^2$ area (1% total perforated area), said openings are spaced 9 mm apart.
T(5%): Perforated layer of 127 openings/cm area (5% total perforated area), said openings are spaced 4 mm apart.

The active layer consisted of a viscose layer of 0.5 mm thickness and a weight of 45 g/m$^2$ (Sawatex® 2611). The overwrap consisted of a non-woven material of 0.05 mm thickness.

SYNGINA Test Procedure

The tampon was weighed before insertion into the SYNGINA. The tampon was thereafter placed in the middle of the condom, and a fluid infusion hose was placed above the inner area of the tampon. Then the chamber was slowly filled with water making a standard pressure on the mantle area of the tampon. The colored fluid was slowly added, and the test was discontinued as the tampon was leaking colored fluid down towards a container. Then, the tampon was weighed once more. As can be seen from table 1 and 2, the absorption of fluid was very similar between the tampons of prior art and the perforated tampons. Thus, the inventive tampons can absorb the same amount of fluid as the tampons of prior art when the fluid has been applied to the insertion end area of the tampons.

TABLE 1

|  | Syngina | | | | |
| --- | --- | --- | --- | --- | --- |
| Tampon | I Conv | II Conv | III T (1%) | IV T (1%) | V T (1%) |
| Filling time (h) | 13:15 | 14:50 | 14:40 | 13:45 | 13:40 |
| Weight before (g) | 2.56 | 2.68 | 3.15 | 3.16 | 3.14 |
| Weight after (g) | 13.06 | 14.67 | 15.03 | 14.09 | 13.86 |
| Absorption (g) | 10.5 | 11.99 | 11.88 | 10.93 | 10.72 |
| Diameter before (mm) | 12.87 | 12.69 | 12.49 | 12.69 | 12.45 |
| Diameter after (mm) | 22.83 | 22.44 | 21.02 | 21.32 | 21.52 |
| Diameter increase (mm) | 9.96 | 9.75 | 8.53 | 8.63 | 9.07 |

TABLE 2

|  | Syngina | | | | |
| --- | --- | --- | --- | --- | --- |
| Tampon | I Conv | II Conv | III T (5%) | IV T (5%) | V T (5%) |
| Filling time (h) | 14:00 | 14.10 | 14:35 | 15:00 | 14:50 |
| Weight before (g) | 2.73 | 2.61 | 3.29 | 3.21 | 3.52 |
| Weight after (g) | 13.57 | 13.58 | 14.47 | 15.01 | 15.02 |
| Absorption (g) | 10.84 | 10.97 | 11.18 | 11.8 | 11.5 |
| Diameter before (mm) | 13.02 | 12.54 | 12.65 | 12.76 | 12.41 |
| Diameter after (mm) | 21.66 | 22.31 | 21.52 | 21.52 | 21.71 |
| Diameter increase (mm) | 8.64 | 9.77 | 8.87 | 8.76 | 9.30 |

Example 3

Method for Measuring the Absorption Rate of the Active Layer

The absorption tests were performed with colored water solution as well as with heparinised human blood. 10 drops were applied with a pipette to the middle of the tampons mantle area. After the fluid entered the tampon and was stabilized, the tampon was cut in halves with a sharp knife. Measurements of the spread of the fluid on the surface and inside of the tampon was performed by a ruler. In addition, the fluid spread was documented by photographs. The fluid spread after 50 drops had been applied on the different tampons was also studied.

No difference was observed regarding the surface spread or depth absorption between the use of colored water and heparinised human blood (results not shown). However, as can be seen from FIG. 5, the spread of the fluid on the surface of the inventive tampons was much more apparent compared to the tampon of prior art. The spread was most apparent in the T(1%) tampon, and a little less in the T(5%) tampon.

Figure 6:
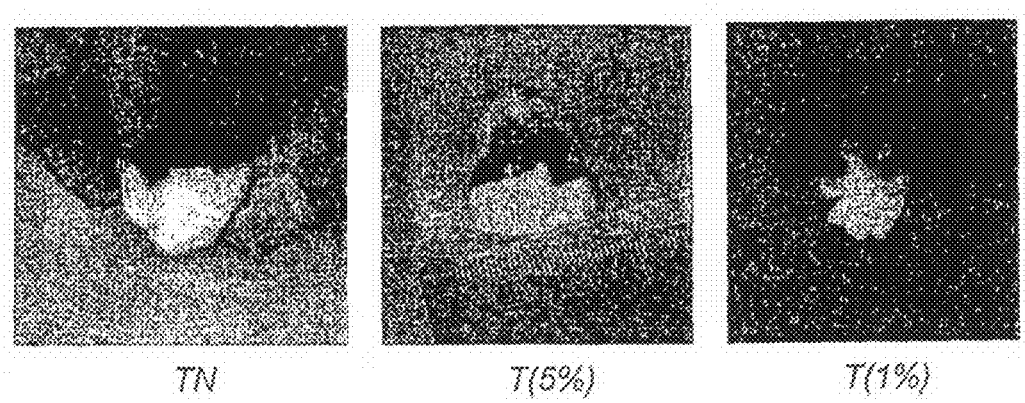
FIG. 6 shows the absorption spread of 10 drops of fluid in the depths of the different tampons. From the left: TN, T(5%), T(1%).

The depth absorption capacity of the different tampons may be observed in FIG. 6. It is clear from this experiment that the inventive tampons have less depth absorption than the tampons of prior art. In the tampon T(1%), a large surface area of absorbed fluid which was outspread around the tampon could be observed in the outer layer of the tampon, thereby providing a moistured surface area against the vaginal tissue. Even the T(5%) tampon had a more outspread surface area of absorbed fluid than the tampon of prior art.

Figure 7:
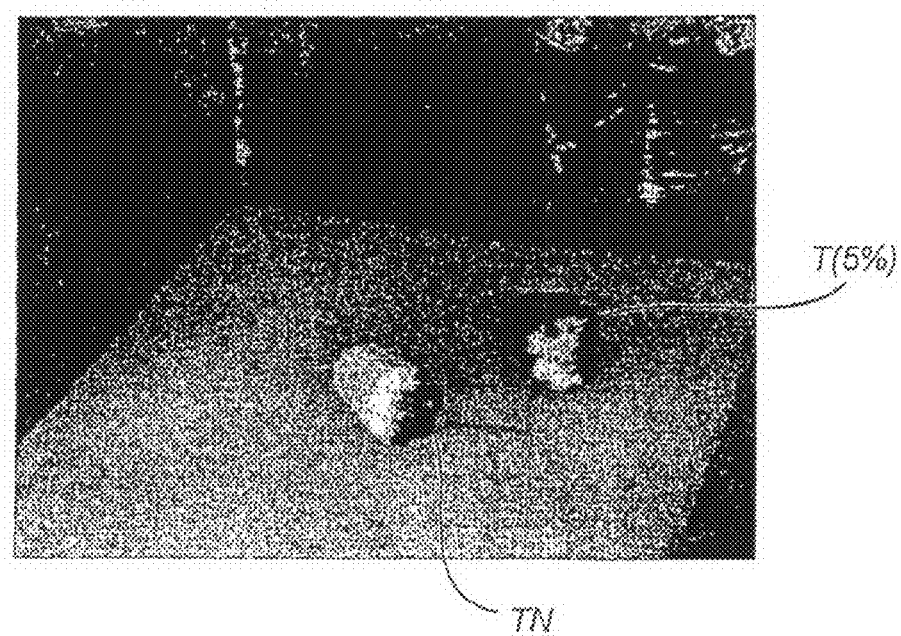
FIG. 7 shows the absorption spread of 50 drops of fluid on the surface of the different tampons. From the left: TN, T(5%).

In FIG. 7, the surface absorption for 50 drops of liquid may be seen. It is apparent that the fluid is more spread over the surface of the inventive tampon.

Moreover, the fluid absorption capacity and the spread of an impregnated lactic acidic composition (PEG 4000, 90%, Na-lactate, 66% 10%) was also measured. Single drops were applied to the sawatex material surface with a pipette, and the spread was observed by ruler measurement. Then, a simple absorption test was performed on a PEG impregnated T(1%). 10 drops of colored solution was applied with the pipette and the spread over the surface, as well as the spread on the depth, was measured with a ruler and documented by photograph.

The impregnation of lactic acid composition proved even to enhance the spread of the fluid on the surface (results not shown).

Example 4

Method for Measuring the Absorption Rate

The tampons were placed in a bowl of colored water. The time for the water to reach the top of the tampon was measured. No difference in the time for the water to reach the top of the tampon was seen between the tampons (results not shown).

Example 5

Comparison of the Effects of the Inventive Tampon with a Tampon of Prior Art

A study was performed in order to compare the inventive tampon with a tampon of prior art ("Apotekets tampon"). The two tampons were compared with regard to non-leakage at the time when the female is bleeding the most, and possible frictional effects, such as difficulties to insert and withdraw the tampon at minor bleeding. The linting of the tampon, as well as leakage of the tampon at movement, were also studied.

The study was performed on women who tested 24 of the prior art tampons, and 32 inventive tampons, both at times of abundant or minor bleeding. The results of the study are presented in the table below.

TABLE 3

| | Inventive tampon (%) | Prior art (%) |
|---|---|---|
| Tampon leaking | 28 | 29 |
| Difficult to insert tampon (minor bleeding) | 19 | 25 |
| Difficult to withdraw tampon | 25 | 26 |
| Tampon linting | 6 | 21 |
| Tampon leaking at movement | 0 | 21 |

As can be seen, the inventive tampon performed just as well as, and even better than, the prior art tampon with regard to leakage of the tampon. As a conclusion, even though the inventive tampon has less superficial absorption capacity as compared to the prior art tampon, it is clear that it performs just as well as, and even better than an ordinary tampon.

In a comparison, the women experienced less discomfort in inserting the inventive tampon at minor bleeding as compared to the prior art tampon.

With regard to the difficulties in withdrawal of the tampon, the women found the inventive tampon to be slightly better than the prior art alternative.

A distinct difference between the two tampons can be seen in the women's perception of the linting of the tampons. 21% of the women experienced the prior art tampon to be linting, while only 6% of the women perceived the inventive tampon to be linting (linting in this application refers to fiber release by the tampon). Linting of the tampon causes irritation of the mucous membrane in the vagina, and may cause micro wounds in the vagina. These micro wounds may lead to an invasion of bacteria, which in turn may lead to an increased risk for the toxic chock syndrome, "TSS". Thus, a lintless tampon is much preferred.

Finally, a major difference is seen in the perception of the women of the tampon leaking at movement. None of the women experienced the inventive tampon to be leaking at movement, while 21% of the women experienced the tampon of prior art to be leaking at movement. As soon as the active layer of the inventive tampon is saturated, the fluid will enter into the absorbent core of the tampon through the partially impermeable layer. However, at movement, the partially impermeable layer will have a low tendency to resubmit the fluid from the absorbent core to the active layer. As a consequence, the inventive tampon does not leak.

As a conclusion, in this clinical test to compare the inventive tampon and a prior art tampon, it is clear that the inventive tampon performed better in all tests as compared to the tampon of prior art.

The invention claimed is:

1. An elongated tampon, comprising:
an absorbent core,
a partially impermeable layer, and
an active layer,
wherein said absorbent core includes a mantle area, an insertion end area, and a withdrawal end area, said partially impermeable layer is arranged on at least a part of said mantle area, said active layer is arranged on at least a part of said partially impermeable layer, and said active layer includes a fluid retaining material,
wherein in use, said partially impermeable layer in combination with said active layer has the ability to provide and maintain a wetted zone of said tampon, said wetted zone being in contact with the body via an optional layer, and said partially impermeable layer contains a plurality of openings, wherein a total sum of area of said plurality of openings constitute 0.5 to 10% of a total area of said partially impermeable layer.

2. A tampon according to claim 1, wherein said partially impermeable layer comprises a plastic foil or a non-woven material.

3. A tampon according to claim 1, wherein said plurality of openings are obtained mechanically.

4. A tampon according to claim 1, wherein said plurality of openings are uniformly distributed over said partially impermeable layer.

5. A tampon according to claim 1, wherein said total sum of the area of said plurality of openings constitute 1 to 5% of the total area of said partially impermeable layer.

6. A tampon according to claim 1, wherein a diameter of one of the plurality of openings is from 0.5 to 3 mm.

7. A tampon according to claim 1, wherein said partially impermeable layer further covers at least a part of said withdrawal end area.

8. A tampon according to claim 1, further comprising an overwrap.

9. A tampon according to claim 8, wherein said overwrap comprises a non-woven material.

10. A tampon according to claim 1, wherein said fluid retaining material is at least one of viscose, a hydrofil non-woven material, or fungi material.

11. A tampon according to claim 1, wherein said active layer comprises an active composition.

12. A tampon according to claim 11, wherein said active composition comprises a carrier.

13. A tampon according to claim 12, wherein said carrier is at least one of polyethylene glycol, hypromellosum and whitepsol.

14. A tampon according to claim 11, wherein said active composition comprises a medical composition.

15. A tampon according to claim 14, wherein said medical composition comprises an acidic substance having a pH of 3.8-4.5.

16. A tampon according to claim 14, wherein said medical composition comprises lactic acid.

17. A tampon according to claim 14, wherein said medical composition comprises an antifungal substance.

18. A tampon according to claim 14, wherein said medical composition comprises at least one of zinc, magnesium, lactoferrin and lactic acid bacteria.

* * * * *